United States Patent
Bosch et al.

(10) Patent No.: US 7,754,139 B2
(45) Date of Patent: Jul. 13, 2010

(54) METHOD FOR PREPARING TRIETHYLENEDIAMINE (TEDA)

(75) Inventors: Marco Bosch, Mannheim (DE); Bernd Stein, Alsbach-Hähnlein (DE); Matthias Frauenkron, Freinsheim (DE); Ulrich Müller, Neustadt (DE)

(73) Assignee: BASF Aktiengesellschaft (DE)

( * ) Notice: Subject to any disclaimer, the term of this patent is extended or adjusted under 35 U.S.C. 154(b) by 136 days.

(21) Appl. No.: 10/559,493

(22) PCT Filed: Jun. 4, 2004

(86) PCT No.: PCT/EP2004/006035

§ 371 (c)(1),
(2), (4) Date: Dec. 5, 2005

(87) PCT Pub. No.: WO2004/108280

PCT Pub. Date: Dec. 16, 2004

(65) Prior Publication Data

US 2006/0116517 A1 Jun. 1, 2006

(30) Foreign Application Priority Data

Jun. 6, 2003 (DE) ................ 103 26 137

(51) Int. Cl.
*B28B 3/20* (2006.01)
(52) U.S. Cl. .................................... 264/677
(58) Field of Classification Search ........... 264/667
See application file for complete search history.

(56) References Cited

U.S. PATENT DOCUMENTS

| | | | |
|---|---|---|---|
| 3,702,886 A | | 11/1972 | Argauer et al. |
| 3,709,979 A | | 1/1973 | Chu |
| 4,582,936 A | * | 4/1986 | Ashina et al. ............... 564/479 |
| 4,966,969 A | * | 10/1990 | Sato et al. ................... 544/352 |
| 5,041,548 A | * | 8/1991 | Sato et al. ................... 544/352 |
| 5,053,374 A | | 10/1991 | Absil et al. |
| 5,280,120 A | * | 1/1994 | King ........................... 544/352 |
| 5,552,035 A | * | 9/1996 | Potter et al. ................. 208/135 |
| 5,731,449 A | * | 3/1998 | Li et al. ....................... 544/352 |
| 5,741,906 A | * | 4/1998 | Santiesteban et al. ....... 544/352 |
| 5,756,741 A | * | 5/1998 | Armor et al. ................ 544/352 |
| 6,084,096 A | * | 7/2000 | Li et al. ....................... 544/352 |
| 6,350,874 B1 | * | 2/2002 | Ogawa ........................ 544/352 |
| 6,555,688 B1 | | 4/2003 | Klockemann et al. |
| 6,562,971 B2 | * | 5/2003 | Frauenkron et al. ......... 544/352 |
| 7,115,742 B2 | * | 10/2006 | Frauenkron et al. ......... 544/352 |
| 7,582,583 B2 | * | 9/2009 | Bosch et al. ................... 502/63 |
| 2002/0072467 A1 | * | 6/2002 | Ogawa .......................... 502/65 |
| 2002/0107394 A1 | | 8/2002 | Frauenkron et al. |
| 2003/0139598 A1 | * | 7/2003 | Frauenkron et al. ......... 544/352 |

FOREIGN PATENT DOCUMENTS

| | | |
|---|---|---|
| EP | 0 130 407 | 1/1985 |
| EP | 0 382 055 | 8/1990 |
| EP | 0 842 936 | 5/1998 |
| EP | 1 192 993 | 4/2002 |
| EP | 1 215 211 | 6/2002 |
| EP | 0 831 096 | 7/2002 |
| EP | 1 382 055 | 1/2004 |
| JP | 3-132061 | 6/1991 |
| WO | WO-91/04943 | 4/1991 |
| WO | WO-01/02404 | 1/2001 |
| WO | WO-02/086946 | 10/2002 |
| WO | WO-03/004499 | 1/2003 |

OTHER PUBLICATIONS

W.T. Reichle, "Reactions of Aliphatic $\alpha$-$\omega$-Diamines in $H^+$-Pentasils", Journal of Catalysis 144, pp. 556-558 (1993).
Ullman's Encyclopedia of Industrial Chemistry, 6th Edition, 2000 Electronic Release, Chapter 3.2.
Ullmann's Encyclopedia of Industrial Chemistry, 6th Edition, 2000 Electronic Release, Chapter 8.3.2.
Ullmann's Encyclopedia of Industrial Chemistry, 6th Edition, 2000 Electronic Release, Chapter 7.6.
Ullmann's Encyclopedia of Industrial Chemistry, 6th Edition, 2000 Electronic Release, Chapter 6.3.2.
Weitkamp, J. et al. (Editors), Catalysis and Zeolites, Fundamentals and Applications, Springer Verlag, Chapter 3.3.3.3, pp. 142-144.
Tanabe, K. et al., "New Solid Acids and Bases, Their Catalytic Properties", Studies in Surface Science and Catalysis, Elsevier, 51 (1989), p. 152.
Huber, G. et al., "Hydrothermal Stability of Co/$SiO_2$ Fischer-Tropsch Synthesis Catalysts", Studies in Surface Science and Catalysis, Elsevier, 139 (2001), p. 423-430.

* cited by examiner

*Primary Examiner*—Steven P Griffin
*Assistant Examiner*—Russell J Kemmerle, III
(74) *Attorney, Agent, or Firm*—Connolly Bove Lodge & Hutz LLP

(57) ABSTRACT

An increase in the cutting hardness of a shaped body comprising a crystalline aluminosilicate is achieved by treating the shaped body with a gas comprising water vapor at from 100 to 600° C. and an absolute pressure of from 0.1 to 10 bar for a period of at least 20 hours, and this shaped body having an increased cutting hardness can be used in processes for chemical synthesis, in particular in a process for preparing triethylenediamine (TEDA) by reaction of ethylenediamine (EDA) and/or piperazine (PIP).

15 Claims, No Drawings

METHOD FOR PREPARING TRIETHYLENEDIAMINE (TEDA)

RELATED APPLICATIONS

This application is a national stage application (under 35 U.S.C. 371) of PCT/EP2004/006035 filed Jun. 4, 2004 which claims benefit to German application 103 26 137.0 filed Jun. 6, 2003.

The present invention relates to a method of increasing the cutting hardness of a shaped body comprising a crystalline aluminosilicate and processes for chemical synthesis in the presence of a crystalline aluminosilicate catalyst, in particular a process for preparing triethylenediamine (TEDA) by reaction of ethylenediamine (EDA) and/or piperazine (PIP).

Chemical and physical properties of crystalline aluminosilicates (zeolites) are, for example, described in general terms in Ullmann's Encyclopedia of Industrial Chemistry, 6th edition, 2000 Electronic Release, chapter 3.2 (also in ref. [46] cited there). In chapter 8.3.2., the possibility of reducing the aluminum content of aluminosilicates by "steaming" at about 600° C. is mentioned; cf. chapter 7.6.

The dealumination of aluminosilicates by "steaming" is also known from Ullmann's Encyclopedia of Industrial Chemistry, 6th edition, 2000 Electronic Release, chapter 6.3.2, and J. Weitkamp et al. (Eds.), Catalysis and Zeolites, Fundamentals and Applications, chapter 3.3.3.3 (pp. 142-144), Springer Verlag, and Studies in Surface Science and Catalysis, vol. 51, "New solid acids and bases", page 152, Elsevier 1989.

It is known from G. W. Huber et al., Studies in Surface Science and Catalysis, vol. 139 (2001), pages 423-430, (table 4, page 427), that the BET surface area of microporous silica ($SiO_2$) decreases significantly after treatment with water vapor and the average pore diameter increases.

EP-A1-130 407 (Nitto) relates to a process for preparing dimethylamine (DMA) from ammonia and methanol using particular zeolite catalysts selected from among mordenite, cliroptilolite and erionite which have been previously brought into contact with water vapor at from 250 to 700° C., preferably for a time of from 10 to 30 hours. In this process, the catalyst activity and selectivity of the reaction to DMA and to monomethylamine and trimethylamine is increased.

EP-A1-1 192 993 (Tosoh Corp.) relates to a process for producing shaped catalyst bodies by mixing particular amounts of amorphous silica having a mean particle size of from 6 to 60 nm with a crystalline aluminosilicate having an $SiO_2/Al_2O_3$ molar ratio of at least 12, and subsequently shaping the mixture in a "molding machine". The shaped bodies produced in this way are said to have a hardness of at least 1 kg.

JP-B-313 20 61 (Tosoh Corp.) describes the sintering of shaped aluminosilicate catalyst bodies at from 500 to 950° C. for at least one hour, e.g. 4 hours in the case of catalyst example 1, in a water vapor atmosphere for increasing the selectivity in the preparation of triethylenediamines and piperazines.

Triethylenediamine (TEDA=DABCO®=1,4-diazabicyclo[2.2.2]octane) is an important intermediate and end product and is used, inter alia, in the preparation of pharmaceuticals and plastics, in particular as catalyst in the preparation of polyurethanes.

There are a large number of synthetic methods for preparing TEDA, which differ mainly in the choice of starting materials and the catalysts used: see, for example, EP-A1 382 055, WO 01/02404, EP-A1-1 215 211 and WO 03/004499.

EP-A1-842 936 (equivalent: U.S. Pat. No. 5,741,906) (Air Products) describes the preparation of TEDA over ZSM-5 zeolites which have been pretreated with a chelating agent. This pretreatment can be combined with "steaming" (page 4, 1st line).

For a further review of the prior art concerning the preparation of TEDA, reference may be made, for example, to EP-A1-1 215 211 (BASF AG).

It is an object of the present invention to discover an improved method of increasing the cutting hardness of a shaped body comprising a crystalline aluminosilicate for use as catalyst in known zeolite-catalyzed reactions, in particular for use as catalyst in a process for preparing triethylenediamine (TEDA) by reaction of ethylenediamine (EDA) and/or piperazine (PIP), which is simple to carry out and results in an increased catalyst operating life and catalyst stability compared to the prior art. At the same time, no deactivation of catalyst should occur as a result of the method and the selectivity in the relevant zeolite-catalyzed reactions, in particular the selectivity to TEDA in the abovementioned process for preparing TEDA, should not be adversely affected.

The cutting hardness of a shaped catalyst body is a measure of its mechanical stability. For industrial applications in known zeolite-catalyzed reactions, including the abovementioned process for preparing TEDA, it is generally desirable for the shaped catalyst body to have a cutting hardness of not less than 9.8 N (corresponding to 1.0 kg), preferably >10 N, in particular >20 N.

We have found that the above object is achieved by a method of increasing the cutting hardness of a shaped body comprising a crystalline aluminosilicate, which comprises treating the shaped body with a gas comprising water vapor at from 100 to 600° C. and an absolute pressure of from 0.1 to 10 bar for a period of at least 20 hours.

The method of the present invention makes it possible for the first time to improve the mechanical properties of a shaped catalyst body, in particular after calcination, and to increase the cutting hardnesses by at least 20%, in particular at least 50%.

The treatment of the shaped body according to the present invention is preferably carried out for a period of at least 50 hours, particularly preferably at least 100 hours.

The treatment of the shaped body according to the present invention is preferably carried out continuously at a WHSV (weight hourly space velocity) of from 0.05 to 5 g, in particular from 0.1 to 1 g, of water vapor per gram of shaped body and per hour ($g_{water\ vapor}/(g_{shaped\ body} \cdot h)$).

The treatment of the shaped body according to the present invention is preferably carried out at from 200 to 450° C., in particular from 300 to 400° C.

The treatment of the shaped body according to the present invention is preferably carried out at an absolute pressure of from 0.1 to 5 bar, in particular from 0.1 to 2 bar.

The shaped body is advantageously fixed in position (fixed bed), e.g. in a tube reactor, during the treatment with water vapor.

The crystalline aluminosilicate in the shaped body preferably has an $SiO_2/Al_2O_3$ molar ratio of greater than 10:1, particularly preferably greater than 50:1, in particular greater than 100:1, especially greater than 200:1, very particularly preferably greater than 400:1. The upper limit of the $SiO_2/Al_2O_3$ molar ratio is generally 2400:1, in particular 2000:1, especially 1200:1.

The crystalline aluminosilicates can be prepared by methods known to those skilled in the art and/or are commercially available.

As consolidating shaping processes for the crystalline aluminosilicates to be used according to the present invention, it is in principle possible to use all methods for achieving appropriate shaping. Preference is given to processes in which shaping is effected by extrusion in customary extruders, for example to give extrudates having a diameter of usually from 1 to 10 mm, in particular from 2 to 5 mm. If binders and/or auxiliaries are required, extrusion is advantageously preceded by a mixing or kneading process. In general, extrusion is followed by calcination steps. The extrudates obtained are comminuted if desired, preferably to form granules or crushed material having a particle diameter of from 0.5 to 5 mm, in particular from 0.5 to 2 mm. These granules or crushed material and shaped catalyst bodies produced in other ways contain virtually no fines having a particle diameter of less than 0.5 mm.

In a preferred embodiment, the shaped body to be used according to the present invention contains up to 80% by weight of binder, based on the total mass of the catalyst. Particularly preferred binder contents are from 1 to 50% by weight, in particular from 3 to 35% by weight. Suitable binders are in principle all compounds used for such purposes, preferably compounds, in particular oxides, of silicon, aluminum, boron, phosphorus and/or zirconium. A binder of particular interest is silicon dioxide, which can be introduced into the shaping process as, inter alia, silica sol or in the form of tetraalkoxysilanes. Further binders which can be used are oxides of beryllium and clays, e.g. montmorillonite, kaolinite, bentonite, halloysite, dickite, nacrite and anauxite.

Examples of auxiliaries for the consolidating shaping processes are extrusion aids; a customary extrusion aid is methylcellulose. Such agents are generally burned out completely in a subsequent calcination step.

The shaped body which is treated by the method of the present invention is particularly preferably calcined beforehand at from 100 to 600° C., in particular from 200 to 450° C., especially from 300 to 400° C. The calcination time is generally at least one hour, preferably from 2 to 24 hours, in particular from 2 to 10 hours. Calcination is carried out in a gas atmosphere comprising, for example, nitrogen, air and/or a noble gas. In general, calcination is carried out in an oxygen-containing atmosphere having an oxygen content of from 0.1 to 90% by volume, preferably from 0.2 to 22% by volume, particularly preferably from 10 to 22% by volume.

In the method of the present invention, the crystalline aluminosilicate in the shaped body is particularly preferably at least partly in the $H^+$ and/or $NH_4^+$ form.

In the method of the present invention, the crystalline aluminosilicate in the shaped body is preferably of the pentasil type, i.e. it has a crystalline skeleton comprising silicon dioxide and aluminum oxide.

The crystalline aluminosilicate, preferably of the pentasil type, is not subject to any additional restrictions in respect of the material or in respect of the process by which it can be obtained.

Examples of crystalline aluminosilicates of the pentasil type which can be treated by the method of the present invention include the following types: ZSM-5 (as disclosed, for example, in U.S. Pat. No. 3,702,886), ZSM-11 (as disclosed, for example, in U.S. Pat. No. 3,709,979), ZSM-23, ZSM-53, NU-87, ZSM-35, ZSM-48 and mixed structures of at least two of the abovementioned zeolites, in particular ZSM-5 and ZSM-11, and also mixed structures thereof.

In the method of the present invention, the shaped body is preferably treated with a gas comprising from 2 to 98% by weight, in particular from 30 to 90% by weight, of water vapor or consisting of water vapor. In a further embodiment, the gas comprises water vapor in the abovementioned amounts and from 2 to 80% by weight, in particular from 10 to 50% by weight, of EDA.

The present invention further relates to processes for chemical synthesis in the presence of a crystalline aluminosilicate catalyst, in which a shaped body whose cutting hardness has been increased beforehand using the method of the present invention is used as catalyst.

The syntheses are, in particular, alkylations (e.g. of aromatics by means of alkenes), disproportionations (e.g. of alkylbenzenes), acylations, isomerizations (e.g. of alkylbenzenes; e.g. the Aris process), oligomerizations, aminations (e.g. hydroaminations or formation of amines from alcohols and ammonia), alkoxylations, epoxidations of alkenes, cyclizations, hydroxylations, condensations, hydrations (e.g. of alkenes) or dehydrations.

Such syntheses are known to those skilled in the art from, for example, G. Perot et al., J. Molecular Catalysis, 61 (1990), pages 173-196, K. Weissermel, H.-J. Arpe, Industrielle organische Chemie, Wiley, 5th ed. 1998, (e.g. pages 365-373), J. Weitkamp, L. Puppe, Catalysis and Zeolites, Springer Verlag, Berlin, 1999, pages 438-538, and R. Eckehart, P. Kleinschmit, Zeolites—Applications of Synthetic Zeolites, Ullmann's Encyclopedia of Industrial Chemistry, 6th edition (electronic), 2000, chapter 7.3.

In particular, we have found a process for preparing triethylenediamine (TEDA) by reaction of ethylenediamine (EDA) and/or piperazine (PIP) in the presence of a crystalline aluminosilicate catalyst, in which a shaped body whose cutting hardness has been increased beforehand by the abovementioned method is used as catalyst.

As regards the way of carrying out the process of the invention for preparing TEDA using the catalyst having an increased cutting hardness which is produced according to the present invention, the teachings of WO 01/02404, EP-A1-1 215 211 and WO 03/004499 are hereby expressly incorporated by reference.

The process of the invention for preparing TEDA can be carried out batchwise or preferably continuously.

The reaction according to the present invention can be carried out in the liquid phase or preferably in the gas phase.

The reaction is preferably carried out in the presence of a solvent or diluent.

Suitable solvents or diluents are, for example, acyclic or cyclic ethers having from 2 to 12 carbon atoms, e.g. dimethyl ether, diethyl ether, di-n-propyl ether or isomers thereof, MTBE, THF, pyran, or lactones such as gamma-butyrolactone, polyethers such as monoglyme, diglyme, etc., aromatic or aliphatic hydrocarbons such as benzene, toluene, xylene, pentane, cyclopentane, hexane, and petroleum ether, or mixtures thereof and, in particular, also N-methylpyrrolidone (NMP) or water or aqueous organic solvents or diluents of the abovementioned type. Ammonia is also suitable as solvent or diluent. Water is particularly preferred as solvent or diluent, in particular as solvent.

When the reaction is carried out in the gas phase, further suitable diluents are inert gases such as nitrogen (e.g. beyond the saturation of the reactor feed) or argon. The reaction in the gas phase is preferably carried out in the presence of ammonia.

For example, the reaction is carried out in the presence of from 2 to 1200% by weight, preferably from 12 to 1200% by weight, in particular from 14 to 300% by weight, very particularly preferably from 23 to 300% by weight, of solvent or diluent, based on EDA used.

For example, the starting mixture used in the process or the reactor feed (=feed stream in the case of a continuous process) comprises from 5 to 80% by weight, preferably from 10 to 80% by weight, particularly preferably from 20 to 70% by weight, very particularly preferably from 20 to 65% by weight, of EDA and from 2 to 60% by weight, preferably from 10 to 60% by weight, particularly preferably from 15 to 60% by weight, in particular from 20 to 50% by weight, of solvent (s) and diluent(s).

In a particular embodiment of the process of the present invention, EDA and one or more amine compounds which each bear a 2-aminoethyl group (—HN—CH$_2$—CH$_2$—) are reacted.

Such amine compounds are preferably ethanolamines (e.g. monoethanolamine (MEOA), diethanolamine (DEOA), triethanolamine (TEOA)), piperazine (PIP), diethylenetriamine (DETA), triethylenetetramine (TETA), tri(2-aminoethyl)amine, morpholine, N-(2-aminoethyl)ethanolamine (AEEA) and piperazine derivatives such as N-(2-hydroxyethyl)piperazine (HEP), N-(2-aminoethyl)piperazine (AEPIP), N,N'-bis (2-aminoethyl)piperazine, N,N'-bis(2-hydroxyethyl)piperazine and N-(2-aminoethyl) -N'-(2-hydroxyethyl)piperazine.

PIP is particularly preferred.

The total amount of these amine compounds present in the reactor feed is, in this particular embodiment, generally from 1 to 1000% by weight, preferably from 3 to 250% by weight, in particular from 7 to 250% by weight, in each case based on EDA used.

For example, the starting mixture used in the process or the reactor feed (=feed stream in the case of a continuous process) contains a total of from 0.5 to 50% by weight, preferably from 2 to 50% by weight, in particular from 5 to 50% by weight, of these amine compounds.

Since the use of MEOA in the starting mixture or in the reactor feed in this particular embodiment can lead to the formation of by-products which are difficult to separate off from the reactor output (=product stream in the case of a continuous process), the content of this amine compound in the starting mixture or reactor feed is preferably from 1 to 50% by weight, based on EDA used.

After the reaction, the products formed are isolated from the reaction product mixture by customary methods, e.g. by distillation and/or rectification; unreacted starting materials can be returned to the reaction.

Thus, PIP present in the reaction product mixture from the process of the present invention can be separated off from this, e.g. by distillation, and returned to the reaction.

An advantage of the process is that intermediate fractions containing both TEDA and piperazine which are obtained in the work-up of the reaction product mixture and fractions comprising, for example, N-(2-hydroxyethyl)piperazine (HEP), N-(2-aminoethyl)piperazine (AEPIP), diethylenetriamine (DETA), triethylenetetramine (TETA), tri(2-aminoethyl)amine and/or N-(2-aminoethyl)ethanolamine (AEEA) can be returned to the reaction.

Furthermore, other amine compounds formed as waste products in other amine cyclization/condensation reactions can be used in the reaction of the present invention without the yields of TEDA being significantly impaired.

In a particularly preferred embodiment, the process of the present invention is carried out, in particular in the case of a continuous process (steady state), using a mixture of EDA and from 14 to 300% by weight of water and from 7 to 250% by weight of PIP, in each case based on EDA, preferably EDA and from 23 to 300% by weight of water and from 8 to 250% by weight of PIP, in each cased based on EDA, particularly preferably EDA and from 33 to 250% by weight of water and from 17 to 250% by weight of PIP, in each case based on EDA, very particularly preferably EDA and from 110 to 185% by weight of water and from 25 to 100% by weight of PIP, in each cased based on EDA, in the reaction.

In this embodiment, the proportion of PIP or of EDA can also be reduced or increased to an extent of from 0.01 to 20% by weight, for example from 0.01 to 10% by weight, in favor of one and at the expense of the other.

For example, the starting mixture used in the process or the reactor feed comprises, in this particularly preferred embodiment, from 10 to 60% by weight of water, from 20 to 70% by weight of EDA and from 5 to 50% by weight of PIP, preferably from 15 to 60% by weight of water, from 20 to 65% by weight of EDA and from 5 to 50% by weight of PIP, particularly preferably from 20 to 50% by weight of water, from 20 to 60% by weight of EDA and from 10 to 50% by weight of PIP, very particularly preferably from 45 to 55% by weight of water, from 30 to 40% by weight of EDA and from 10 to 30% by weight of PIP, where the proportion of PIP or of EDA can be reduced or increased to an extent as described above in favor of one at the expense of the other.

In this particularly preferred embodiment of the process, the reactor feed preferably contains less than 10% by weight, particularly preferably less than 5% by weight, in particular less than 2% by weight, of further components in addition to EDA, PIP and water.

In this particularly preferred embodiment, the reaction can, in particular in the case of a continuous process (in the steady state), be carried out at the abovementioned ratios or amounts of starting materials in such a way that EDA is converted virtually completely (i.e. conversion greater than 95%, in particular greater than 97%) into TEDA and PIP with a selectivity greater than 90%, in particular greater than 95%.

In the process, the EDA/PIP ratio in the reactor feed (=feed stream in the case of a continuous process) is preferably set within the abovementioned ranges so that the consumption of PIP tends toward zero (e.g. from 0 to 30 kg, in particular from 0 to 15 kg, very particularly preferably from 0 to 10 kg, per 100 kg of TEA in the reaction product mixture), in particular is zero, in the overall balance as a result of PIP being separated off from the reaction product mixture and being recirculated to the reactor feed, and at the same time the EDA used is reacted completely (>95%, in particular >97%, very particularly preferably >99%). This means that essentially no additional PIP is supplied to the process during continuous operation.

Since the amount of EDA discharged tends toward zero in such a mode of operation, the fractionation of the reactor output, e.g. by distillation and/or rectification, is particularly simple in this process variant.

The reaction temperature in the process of the present invention is preferably from 270 to 400° C., particularly preferably from 310 to 390° C., in particular from 310 to 350° C.

The starting components or the reactor feed are advantageously preheated.

Furthermore, the following reaction conditions have been found to be advantageous in carrying out the process:

a WHSV (weight hourly space velocity) based on amines used in the reaction of from 0.05 to 6 h$^{-1}$, preferably from 0.1 to 1 h$^{-1}$, particularly preferably from 0.3 to 1 h$^{-1}$, and a pressure (absolute) of from 0.01 to 40 bar, in particular from 0.1 to 10 bar, preferably from 0.8 to 2 bar.

Suitable reactors in which the process of the present invention can be carried out are stirred vessels and in particular tube reactors and shell-and-tube reactors. The zeolite catalyst is preferably present as a fixed bed in the reactor.

The reaction in the liquid phase can be carried out, for example, in the suspension mode, the downflow mode or the upflow mode.

The preferred reaction in the gas phase can be carried out in a fluidized bed of catalyst or preferably in a fixed bed of catalyst.

The way in which the process of the present invention can be carried out is additionally described by way of example in the following paragraph:

The reactor feed (composition: as described above) is brought into the gas phase in a vaporizer, which may be part of the actual reactor, at 250-500° C. and passed over the catalyst. The reaction product mixture obtained in gaseous form at the reactor outlet is quenched at 20-100° C., preferably 80° C., by means of liquefied reaction product mixture circulated by pumping. This liquefied reaction product mixture is worked up as follows: in a first distillation stage, low boilers such as acetaldehyde, ethylamine, ammonia and water and also heterocyclic compounds which are formed as secondary components in the synthesis are separated off. In a second distillation stage, the reaction product mixture is freed of piperazine which is recirculated to the reactor feed. The stream of piperazine which has been separated off can contain up to 20% by weight of TEDA. (As an alternative, water and piperazine can be separated off simultaneously and be recirculated together to the reactor feed). In a third distillation stage, the desired TEDA product is isolated from the reaction product mixture by distillation and, if necessary, worked up further, e.g. in a subsequent crystallization stage (e.g. as described below).

EXAMPLES

The cutting hardnesses were measured on an apparatus from Zwick (model: BZ2.5/TS1S; prestressing force: 0.5 N, prestressing speed: 10 mm/min.; test speed: 1.6 mm/min.) and are the means of in each case 10 measured catalyst extrudates.

The detailed procedure for determining the cutting hardness was as follows:

Extrudates were loaded by a cutter having a thickness of 0.3 mm with increasing force until the extrudate had been cut through. The force necessary for this is the cutting hardness in N (Newton). The determination was carried out on a testing apparatus from Zwick, Ulm, having a fixed rotatable plate and a freely movable, vertical punch having a built-in cutter having a thickness of 0.3 mm. The movable punch with the cutter was connected to a load cell for recording the force and during the measurement moved toward the fixed rotatable plate on which the extrudate to be measured was located. The testing apparatus was controlled by a computer which recorded and evaluated the measured results. 10 straight, where possible crack-free extrudates having a mean length of from 2 to 3 times the diameter were taken from a well-mixed catalyst sample, their cutting hardnesses were determined and subsequently averaged.

In the following tables of results, the weight hourly space velocity (WHSV) is reported in g of EDA+PIP (=$g_{org}$) per g of catalyst and per hour.

The EDA/PIP/H$_2$O ratio is by weight (% by weight).

The modulus is the molar SiO$_2$/Al$_2$O$_3$ ratio.

C=conversion in % by weight based on the amount of the material (EDA or PIP) indicated in the table used; S=selectivity of the reaction to the indicated product based on reacted —CH$_2$—CH$_2$— units from EDA and PIP.

Table 1 below shows results from experiments on the reaction of gaseous ethylenediamine/piperazine/water mixtures to form triethylenediamine (TEDA). It can be seen that the "catalysts removed from the reactor" A and B have a significantly increased cutting hardness compared to the catalyst installed. Within the limits of measurement accuracy (+/− 1%), the increase in the cutting hardness is not associated with any deactivation and the selectivity to TEDA remains the same.

TABLE 1

| Cat.[a] | Extrudate Ø [mm] | Time [h] | Hardness[d] [N] | C (EDA) [%] | S (TEDA) [%] |
|---|---|---|---|---|---|
| A | 1.9[b] | 0 | 12 | 95 | 94 |
|   |   | 410 | 27 | 94 | 93 |
| B | 2.1[c] | 0 | 11 | 95 | 88 |
|   |   | 500 | 38 | 95 | 87 |

[a]H-ZSM-5, modulus 1000;
[b]20% by weight of SiO$_2$ as binder;
[c]26% by weight of SiO$_2$ as binder;
[d]cutting hardness.
Test conditions: WHSV = 0.50 $g_{org}$/($g_{cat}$h); T = 350° C.; EDA/PIP/H$_2$O = 25/25/50.

Table 2 below shows experimental results on the mechanical properties of the catalyst C (H-ZSM-5, modulus 1000, 20% by weight of SiO$_2$ as binder, extruded) after treatment with water vapor at 350° C. [WHSV =0.3 $g_{water\ vapor}$/($g_{cat}$h)]. There is a significant increase in the cutting hardness of the shaped catalyst bodies from 16 to 26 N after 259 hours (h). After 452 h, the cutting hardness is 28 N. The performance of this catalyst in the synthesis of TEDA [C(EDA), C(PIP) and S(TEDA)] remains unchanged compared to the initial values within measurement accuracy (+/−1 %).

TABLE 2

| Cat.[a] | Extrudate Ø [mm] | Binder[b] [% by wt.] | Time [h] | Hardness[c] [N] | C (EDA) [%] | S (TEDA) [%] |
|---|---|---|---|---|---|---|
| C | 1.9 | 20 | 0 | 16 | 95 | 92 |
|   |   |   | 259 | 26 | — | — |
|   |   |   | 452 | 28 | 95 | 91 |

[a]H-ZSM-5, modulus 1000;
[b]SiO$_2$;
[c]cutting hardness;
test conditions: WHSV = 0.50 $g_{org}$/($g_{cat}$h); T = 350° C.; EDA/PIP/H$_2$O = 25/25/50.

Table 3 below shows experimental results for the water vapor treatment [T=350° C., WHSV=0.3 $g_{water\ vapor}$/$g_{cat}$h] of catalyst extrudates based on ZrO$_2$ as binder material (cat. D). As can be seen, an increase in the cutting hardness from 2.6 N to 3.6 N can be achieved by means of the method of the present invention under the conditions described in the case of ZrO$_2$ as binder material (=binder).

TABLE 3

| Cat.[a] | Binder[b] | Extrudate Ø [mm] | Time [h] | Hardness[c] [N] | Increase [%] |
|---|---|---|---|---|---|
| D | ZrO$_2$ | 1.9 | 0 | 2.6 | — |
|   |   |   | 72 | 3.0 | 15 |
|   |   |   | 262 | 3.6 | 38 |

[a]H-ZSM-5, modulus 1000;
[b]20% by weight of binder;
[c]cutting hardness.

The experimental results in table 4 below show that the increase in the cutting hardness achieved by means of the method of the present invention is not restricted to the use of H-ZSM-5 as active components of a shaped catalyst body. For example, a catalyst consisting of 80% by weight of H-mordenite [Si/Al ratio=7.8] and 20% by weight of SiO$_2$ (cat. E) displays a significant increase in the cutting hardness after (in this case) 50 h under the treatment conditions [T=350° C. and WHSV=0.3 $g_{water\ vapor}/g_{cat}h$].

TABLE 4

| Cat.[a] | Binder[b] | Extrudate Ø [mm] | Time [h] | Hardness[c] [N] | Increase [%] |
|---|---|---|---|---|---|
| E | SiO$_2$ | 1.7 | 0 | 6.3 | — |
|   |   |   | 50 | 9.1 | 44 |
|   |   |   | 100 | 12.4 | 97 |

[a]H-mordenite, modulus 7.8;
[b]in each case 20% by weight of binder;
[c]cutting hardness

We claim:

1. A process for preparing triethylenediamine (TEDA) by reaction of ethylenediamine (EDA) and/or piperazine (PIP) in the presence of a crystalline aluminosilicate catalyst, wherein a shaped body whose cutting hardness has been increased beforehand using a method of increasing the cutting hardness of a shaped body comprising a crystalline aluminosilicate having an SiO$_2$/Al$_2$O$_3$ molar ratio of 10:1 to 1200:1, wherein the shaped body comprises a binder selected from among oxides of silicon and/or zirconium and is treated with a gas consisting of water vapor at from 100 to 600° C. and an absolute pressure of from 0.1 to 10 bar for a period of at least 20 hours and the shaped body has been calcined at from 100 to 600° C. before the treatment with water vapor is used as the catalyst.

2. The method according to claim 1, wherein the shaped body is treated for a period of at least 50 hours.

3. The method according to claim 1, wherein the shaped body is treated continuously at a WHSV (weight hourly space velocity) of from 0.05 to 5 g of water vapor per gram of shaped body and per hour ($g_{water\ vapor}/(g_{shaped\ body} \cdot h)$).

4. The method according to claim 1, wherein the shaped body is treated continuously at a WHSV (weight hourly space velocity) of from 0.1 to 1 g of water vapor per gram of shaped body and per hour ($g_{water\ vapor}/(g_{shaped\ body} \cdot h)$).

5. The method according to claim 1, wherein the shaped body is treated at from 200 to 450° C. and an absolute pressure of from 0.1 to 2 bar.

6. The method according to claim 1, wherein the shaped body is fixed in position (fixed bed) during the treatment with water vapor.

7. The method according to claim 1, wherein the crystalline aluminosilicate in the shaped body has an SiO$_2$/Al$_2$O$_3$ molar ratio of greater than 50:1.

8. The method according to claim 1, wherein the crystalline aluminosilicate in the shaped body is at least partly in the H$^+$ and/or NH$_4^+$ form.

9. The method according to claim 1, wherein the crystalline aluminosilicate in the shaped body is of the pentasil type.

10. The process according to claim 1, wherein the reaction is carried out continuously and in the gas phase.

11. The process according to claim 1, wherein EDA and one or more amine compounds selected from the group consisting of monoethanolamine, diethanolamine, triethanolamine, PIP, diethylenetriamine, triethylenetetramine, tri(2-aminoethyl)amine, morpholine, N-(2-aminoethyl)ethanolamine, N-(2-hydroxyethyl)piperazine, N-(2-aminoethyl)piperazine, N,N'-bis(2-aminoethyl)piperazine, N,N'-bis(2-hydroxyethyl)piperazine and N-(2-aminoethyl)-N'-(2-hydroxyethyl)piperazine are reacted.

12. The process according to claim 1, wherein EDA and from 7 to 250% by weight of piperazine (PIP), based on EDA, are reacted.

13. The process according to claim 1, wherein EDA, from 8 to 250% by weight of PIP and from 23 to 300% by weight of water, in each case based on EDA, are reacted.

14. The process according to claim 1, wherein the reaction temperature for the reaction to form TEDA is from 310 to 390° C.

15. The process according to claim 1, wherein the absolute pressure in the reaction to form TEDA is from 0.1 to 10 bar.

* * * * *